(12) United States Patent
Ramsey

(10) Patent No.: US 6,589,545 B1
(45) Date of Patent: Jul. 8, 2003

(54) METHOD OF CONTROLLING INSECT INFESTATION

(76) Inventor: Bruce R. Ramsey, 3600 Higgins Dr., Norton, OH (US) 44203-5527

( * ) Notice: Subject to any disclaimer, the term of this patent is extended or adjusted under 35 U.S.C. 154(b) by 0 days.

(21) Appl. No.: 09/687,900

(22) Filed: Oct. 13, 2000

Related U.S. Application Data

(63) Continuation-in-part of application No. 09/480,295, filed on Jan. 10, 2000, now abandoned, which is a continuation-in-part of application No. 09/386,747, filed on Aug. 31, 1999, now abandoned.

(51) Int. Cl.$^7$ .............................................. A01N 25/34
(52) U.S. Cl. ........................ 424/409; 424/406; 424/407; 424/411; 424/413; 424/414; 514/531
(58) Field of Search .......................... 514/531; 424/405, 424/409, 417, 411, 412, 413, 406, 407, 414

(56) References Cited

U.S. PATENT DOCUMENTS

| | | | | |
|---|---|---|---|---|
| 4,921,703 A | * | 5/1990 | Higuchi et al. ............. | 424/419 |
| 5,925,368 A | * | 7/1999 | Van Voris .................... | 424/405 |
| 5,985,304 A | | 11/1999 | Van Voris et al. | |

FOREIGN PATENT DOCUMENTS

| WO | 97/47190 | 12/1997 |
|---|---|---|

OTHER PUBLICATIONS

Blumenthal et al J. Econ. Entomol. 79(5) 1394–96, 1986.*
Jann Suszkiw, "Gypsy Moth War's Battle of the Burlap," Agricultural Research, Agricultural Research Service, vol. 47 (No. 4), Apr. 1999, (1 page).

G.B. White, R.E. Webb, and K.W. Thorpe, "Forest and Shade Trees—Evaluation of an Insecticidal Latex Coating for Control of Late–Stage Gypsy Moth Larvae, 1997," Arthropod Management Tests, Entomological Society of America (Lanham, MD), vol. 24, Jul. 20, 1999, p. 385 (2 pages).
"Super IQ Insecticide Coating APT Clear Finish"—Specimen by BioDyne Americas Corporation, Bellevue, WA (1 page).
"Super IQ Insecticide All Purpose Transparent Coating (APT)"—Materials Safety Data Sheet, by BioDyne Americas Corporation, Mercer Island, WA (Jul. 16, 1990, revised as of Jan. 1, 1994) (2 pages).
John Douglas, "Groundline Repair for Wood Poles," EPRI Journal, Apr./May 1986, p. 28–31 (4 pages).
Caroline Cox, "Permethrin: Insecticide Fact Sheet," Journal of Pesticide Reform, Summer 1998, vol. 18, No. 2141, taken from web site safe2use.com/poisons–pesticides/pesticides/permethrin/cox–report/cox.htm (7 pages).

* cited by examiner

Primary Examiner—Neil S. Levy
(74) Attorney, Agent, or Firm—Robert J. Clark; Hahn Loeser & Parks, LLP

(57) ABSTRACT

The present invention relates to a method of controlling insect infestation whereby an insecticidal coating having an extended residual period of a few months to a year is applied to a surface. A removable cover may be positioned near the surface to create a substantially darkened region to exploit some insects' natural tendencies to hide in dark places during daylight hours. Alternatively, the insecticide may be applied prior to the hatching of the insect eggs to control the population upon hatching. The method is especially effective for controlling the presence of gypsy moth caterpillars on trees. The present method may be accomplished by covering a portion of a tree trunk with an insecticidal coating containing an active ingredient such as chlorpyrifos, pyrethroid, permethrin, or tralomethrin and covering the coated area with burlap. In addition, the method of the present invention can be used to control the presence of insects on the sides of houses or other structures.

15 Claims, 1 Drawing Sheet

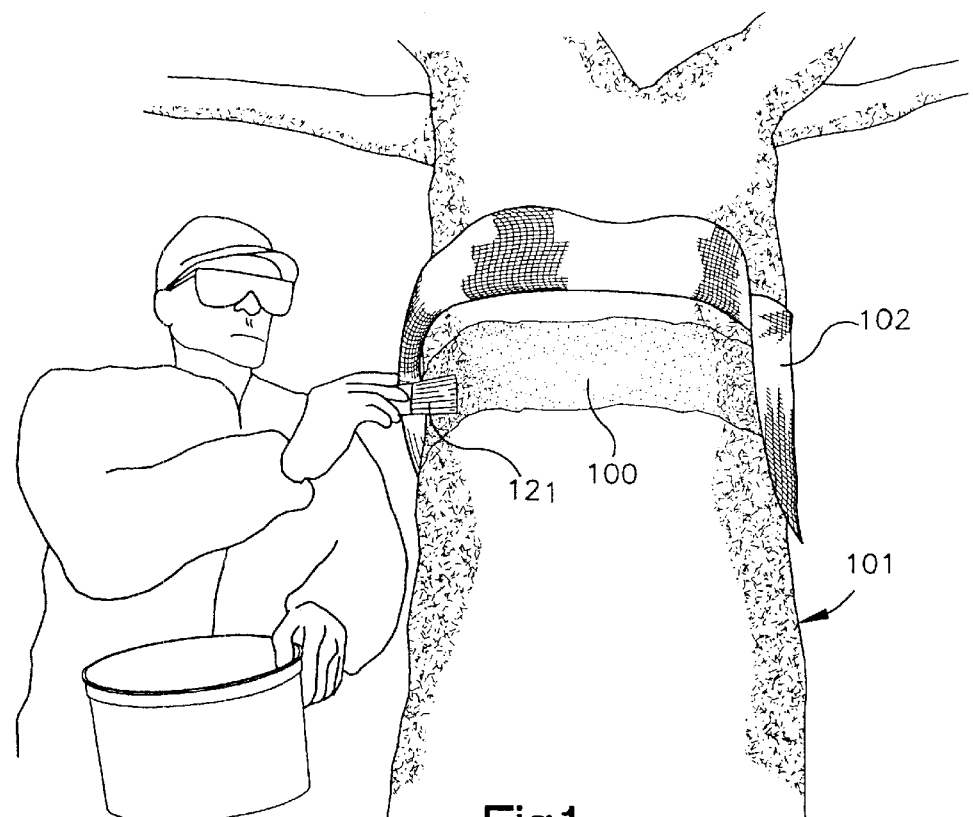
Fig.1
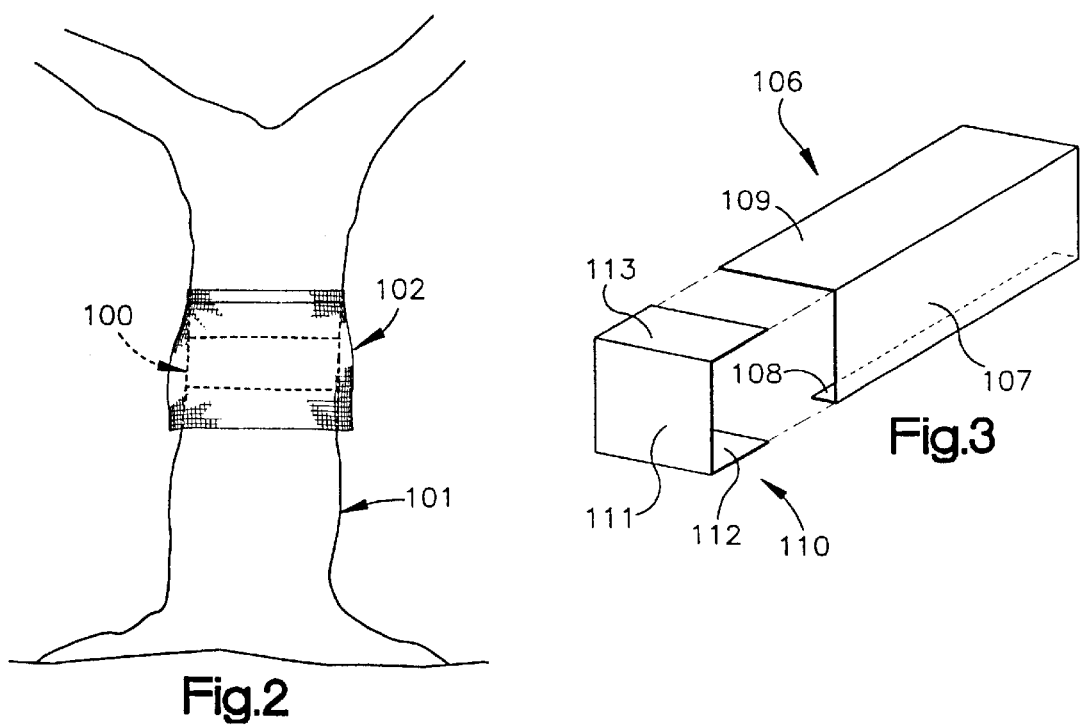
Fig.2
Fig.3

METHOD OF CONTROLLING INSECT INFESTATION

This application is a continuation-in-part of application Ser. No. 09/480,295, now abandoned filed Jan. 10, 2000, which is a continuation-in-part of application Ser. No. 09/386,747 filed Aug. 31, 1999 now abandoned. The present invention relates to a method of controlling insect infestation. The present method involves coating at least a portion of a surface with an insecticide so that insects that crawl over the surface will encounter the insecticide. The present method may also include covering the treated area to create a dark region, thereby exploiting certain insects' natural tendency to hide in dark places during daylight hours.

TECHNICAL FIELD

BACKGROUND OF THE INVENTION

For years, insects such as gypsy moth caterpillars or larvae have plagued homeowners, golf course owners, park caretakers and others in various parts of the United States. Large numbers of these insects will hide during the day, to avoid the heat and predators such as birds. At night, however, they emerge from their dark hiding places to feed on the leaves of trees, often destroying the foliage. The insects also crawl onto the sides of homes or other structures such as standing mailboxes, doghouses, sheds, flagpoles, or any vertical structures upon which insects might crawl. The mere presence of these insects on the structure is an annoyance, but in addition, the pests leave their feces on the structure. In large numbers, these pests can leave an unsightly mess on the side of the structure.

In recent years, several mechanical methods have been attempted to remove the pests from trees. These include placing sticky barriers or burlap sacks around tree trunks, so that the insects can be easily removed. Once the insects are trapped by the sticky barrier, a person can kill them by knocking the pests off the tree into a bucket of bleach, soapy water or some other agent. However, those pests stopped by a burlap sack must be removed before dusk, because when the sun goes down, the pests emerge to attack the leaves. This is often inconvenient for homeowners, especially those with large yards filled with trees. Ridding the trees of the insects before dusk requires that a person hurry home from work and quickly attend to the trees before dinner so as not to risk more damage to the foliage. In addition, the sticky barriers must be closely monitored, because any debris deposited thereon could become a bridge that the pest could use to cross the barrier and reach the leaves.

As yet, no one has attempted to apply a pest killing agent along with these mechanical barriers to protect the leaves. In addition, no one has created a method to control the gypsy moth population prior to or immediately after the hatching of the caterpillar eggs.

Further, certain types of insecticidal coatings are not only extremely effective at killing pests, but also have a long residual period, such that the coatings only need to be applied to a surface once per season or per year. The residual period may be a month to a year or more. Such coatings use active ingredients including but not limited to chlorpyrifos, pyrethroid, permethrin and tralomethrin.

SUMMARY OF THE INVENTION

It is an object of the present invention to provide an improved method of controlling insect infestation by applying an effective insecticidal coating having an extended residual period to a surface and covering the coating with a removable cover to create a dark region for insects to hide. The residual period may be a month to a year or more. Insecticidal agents which may be contained in the coating used in the present method include but are not limited to chlorpyrifos, pyrethroid, permethrin, and tralomethrin.

In one embodiment of the present invention, the insecticidal coating is applied to trees to control gypsy moth caterpillars. The coating may be applied at various times such as just prior to or immediately after the gypsy moth eggs hatch or any time after hatching to protect trees and/or surfaces. The insecticidal coating is covered with a piece of burlap or other opaque material that is adhered to the tree. The method exploits the habits of these particular caterpillars that hide in dark places during the day, only to emerge at dusk to destroy leaves and other foliage. The caterpillars will crawl under the burlap coating to hide for the day. Once there, they will encounter the insecticidal coating. The insects will die then fall off the tree.

In another embodiment of the present invention, the insecticidal coating is applied to the base of a house or other structure. The coated area is then covered to create a darkened region. Once under the shelter of the covering, the insects encounter the insecticidal coating and die.

In another embodiment, at least a portion of a surface where gypsy moth egg masses are located may be treated with insecticide. When the caterpillars hatch from the eggs they will crawl over the insecticide treated area and die.

BRIEF DESCRIPTION OF THE DRAWINGS

FIG. 1 illustrates one possible method of application of insecticide to a surface.

FIG. 2 illustrates a covering comprised of an opaque material as applied to a tree trunk.

FIG. 3 shows a perspective view of an insecticide structure barrier.

DETAILED DESCRIPTION OF THE INVENTION

In the following detailed description of the preferred embodiments of the present invention, reference is made to the accompanying drawings which, in conjunction with this detailed description, illustrate and describe a method for controlling insect infestation.

In the present invention, the method of controlling insect infestation is comprised of the steps of using a insecticidal coating with an extended residual period to coat a surface. The residual period may be approximately several months to one year or longer in time. Preferably the insecticidal coating contains an active ingredient such as chlorpyrifos, pyrethroid, peremethrin, or tralomethrin. Preferred types of insecticides are those that act as neurotoxins on insects.

The pesticides used in a preferred embodiment of the present invention are neurotoxins to insects. For instance, the insecticide permethrin blocks the flow of sodium ions into nerve cells thereby over-exciting the nervous system of the insect. When this happens the nervous system malfunctions: in response to a single stimulus to a sense organ, nerves send a group of impulses rather than a single impulse. Other insecticides which act in different ways on the biological functions of an insect can be as effective when used in the present invention. The above description is intended as example only.

One benefit of an insecticide with a long residual period is that after the insecticidal coating is applied, it will remain effective for a long period and only needs to be reapplied to the surface approximately once per season or once per year. One such insecticidal coating is sold under the trademark SUPER IQ™. The SUPER IQ™ product contains chlorpyrifos as an active ingredient. Another such insecticidal coating, which is a preferred embodiment of the present invention, is comprised of an insecticide formulated using permethrin as the active ingredient in a concentration of two percent of the volume of the total pesticide solution. Although it is preferred to use an insecticial coating with an extended residual period of at least a month or more, thus making application more convenient, it is contemplated by the present invention that insecticidal coatings with shorter residual periods can be used. However, coatings with shorter residual periods must be applied to surfaces more frequently.

The insecticidal coating in one embodiment is in a liquid form and is applied to the surface with a paintbrush 121 as shown in FIG. 1. The surface is not limited to trunks of trees, but may include the outer surfaces of sides of homes, sheds, doghouses, standing mailboxes, flagpoles and many other structures. It may be preferred for the insecticidal coating applied in this way to have a high viscosity so that when it is applied with an implement such as a paintbrush a substantial amount of insecticide does not run down the trunk or surface. This method of application also avoids broadcasting the insecticidal substance to surrounding areas. However, it is contemplated by the present invention that other modes of application could be used including sponges, or roller brushes. Additionally, the insecticide may be applied by spraying it onto the surface. If so, the insecticide formulation may require a lower viscosity than those which are applied by the other methods mentioned. The coating may be sprayed on to the surface by any known method such as a pump garden sprayer, an aerosol can, through a sprayer nozzle on a bottle, or any other known modes of spraying liquids onto surfaces.

The insecticide may be applied to trees near gypsy moth egg masses on the trunks or branches. When the caterpillars hatch from the eggs, they will crawl over the area treated with insecticide and be killed. Applying the insecticide prior to hatching will act as a type of pre-emptive strike to prevent damage from the gypsy moth caterpillars. However, the present method is also effective to protect trees and other surfaces if the insecticide is applied after the caterpillars hatch. In this situation, the method of the present invention will prevent damage by the existing caterpillar or insect population.

Following application to the surface, the insecticide coating is allowed to dry. A cover is removably positioned over or against an area of the surface where the insecticide coating has been applied to create a substantially darkened or shaded region.

In one embodiment of the present invention, the insecticidal coating 100 is applied to at least a portion of a surface of a trunk 101 of a tree or other plant. A cover 102 may then be removably positioned over the coated region. A layer of opaque fabric 102, preferably burlap, is secured to the trunk of the plant 101. The fabric 102 can be secured on the trunk 101 by a variety of methods including staples, nails, rope, twine, tape or glue. The piece of fabric 102 used is dimensioned to fit the particular plant being treated. The piece of fabric 102 should be long enough to fit around the width of the trunk 101 of the plant. In addition, the piece of fabric 102 should have a width to cover the band of insecticide 100 applied to the trunk 101, usually about 8 to 12 inches wide.

In the present method, the fabric 102 is loosely secured to the trunk 101 at its top margin and tightly secured to the trunk at the bottom margin. The insecticidal coating 100 is applied to the trunk 101 to form a band around the trunk about 8 to 12 inches wide starting at the bottom margin of the fabric 102. The band of insecticidal coating 100 is allowed to dry overnight. After the coating 100 dries, the top margin of the fabric 102 is released to fall loosely over the band of insecticidal coating 100 on the trunk 101 as shown in FIG. 2. Insects that crawl under the fabric 102 covering during the day, where they come in contact with the insecticidal coating 100. The insects die and fall off the trunk 101.

Although burlap is a preferred fabric to use as a covering in this embodiment of the present invention, it is contemplated that any opaque material which creates a suitably dark region on the trunk of the plant can be secured to the tree as a covering for the method described herein.

In another embodiment, the insecticidal coating is applied to an outer surface of a house or other structure. In a preferred embodiment, the coating is applied at the base of the structure. After the coating dries, the area is covered to create a darkened region. Methods of covering include leaning a board against the structure or releasably securing a piece of opaque material to the structure. Insects that may attempt to crawl up the side of the structure will encounter the insecticidal coating and die.

FIG. 3 shows a barrier generally designated 106 for covering an area of a structure in the present invention. The barrier 106 is comprised of a flat back portion 107, a first flat side portion 108, and a second flat side portion 109. The side portions 108, 109 are connected at each edge of the width of the back portion 107 and extend outwardly from the back portion 107 of the barrier. The side portions 108–109 are preferably the same length as the back portion 107 of the barrier. In one embodiment of the present invention one of the side portions 109 is longer than the other side portion 108. When the barrier is positioned relative to a structure, one side portion 108 is placed flush against the ground or floor so that the other side portion 109 creates a shaded region at the base of the structure. In the situation where one side 109 is longer than the other side 108, the shorter side 108 is placed against the ground. In this way, the longer side portion 109 of the barrier creates a shaded region of the ground.

In a preferred embodiment, the barrier 106 is constructed of an opaque, rigid material such as wood, metal or plastic, although less rigid material such as cardboard could be used. This list of materials is intended as example only, and should not be considered to limit the barrier to any particular material.

End caps may be used to close off each end of the length of barrier 106 to create a substantially darkened region at the base of the structure. End caps 110 are comprised of a center portion 111 and side portions 112–113, which are connected at opposite ends of the center portion 111. The end caps 110 can be placed at either or both ends of the back portion 107 of the barrier 106. End caps 110 are positioned so that a first side portion 112 is flush against the ground or floor and a second side portion 113 is positioned either above or below barrier side 109 which creates the shaded region. Alternatively, the end caps may be comprised of a flat structure such as a board which may be leaned against the ends of the length of the barrier to create the substantially darkened region.

The inside and/or backside of the barrier 106 and/or end caps 110 may be coated with an insecticidal coating having a long residual period. The barrier 106 is then placed against a structure as described above. Insects will crawl into or behind the barrier 106 and will encounter the insecticide and die. Alternatively, the base or a portion of the structure may be coated with the insecticidal coating. The barrier 106 is then placed against the structure. Insects that crawl into or behind the barrier 106 will encounter the insecticide on the structure and die.

It should be noted that the end caps 110 are not necessary for this embodiment of the invention to be effective. The barrier alone may create a suitable darkened region to attract insects.

Control of gypsy moth caterpillars may also be affected by the timing of the application of the pesticide composition to surfaces, although it is contemplated that insecticides in the present invention may be applied at any time during the season when gypsy moths and their larvae are active. In conjunction with the above described embodiments of the present method or independently, the insecticide may be applied to a region where gypsy moth egg masses are located. In this way, as soon as the gypsy moth caterpillars hatch and crawl away from the egg mass, they will encounter the insecticide and die. In addition, if a pesticide with a residual period of approximately several months is applied, a single application prior to the hatching of the eggs may control the gypsy moths in a treated region for an entire season. However, the present invention is intended to cover pesticides which may require more frequent applications.

In another embodiment of the present invention, insecticide having an extended residual period of a few months to a year or more is applied to various surfaces including, but not limited to tree trunks, tree limbs, or surfaces of various structures near where gypsy moth egg masses are located. The insecticide is applied at a time prior to or shortly following the hatching of the gypsy moth caterpillar eggs. The insecticide may be applied by a paintbrush, roller, sponges or by spraying on to the surfaces. In this embodiment once the caterpillars hatch from the eggs, they will crawl away from the egg masses, over the area treated with pesticide. The insecticide will kill the caterpillars. This method can provide control of the gypsy moth caterpillar population before the insects have a chance to cause any damage to trees or other surfaces.

The invention has been described with reference to several embodiments. Obviously, modifications and alterations will occur to others upon the reading and understanding of the specification. It is intended to include all such modifications and alterations insofar as they come within the scope of the appended claims or the equivalents thereof.

EXAMPLE 1

A group of 10 oak trees was selected. The group consisted of 5 pairs of White Oaks and 5 pairs of Red Oaks. As shown in FIG. 1, burlap was adhered to all trees with twine and staples at the top portion of the burlap 102. A ¾ cm width inner flap was formed at the top margin of the burlap flush against the tree by folding the top margin of the burlap. An outer flap with a 20 cm width was formed which hung away from the tree trunk. Using approximately 900 ml of an insecticidal coating containing chlorpyrifos (in a form sold under the name SUPER IQ™), 10 trees were coated with a nylon bristle paintbrush to form a continuous 20 cm band around the tree trunk 101. The band of chlorpyrifos insecticidal coating overlapped the inner band of the burlap. The outer flap of the burlap was pinned up during the application and drying of the chlorpyrifos insecticidal coating. After the bands dried for 24 hours, the flaps were allowed to hang over the band of insecticidal coating. Control group trees were not coated with insecticide and had only burlap collars.

The insects used in the test were gypsy moth caterpillars, which were raised on a wheat germ based diet to the fourth instar. Equal numbers of caterpillars (5–8 depending on availability) were placed on the exposed and untreated bark of the trees, below the burlap collars. The caterpillars were confined to a restricted area of the tree trunk by sticky barriers placed 30 cm above and 30 cm below the burlap 102. The caterpillars were allowed to migrate within this restricted range. The length of exposure time for the caterpillars ranged from 4.5 to 7 hours with an average time of 5.9 hours.

After the exposure period, the caterpillars were removed from the trees and placed in diet cups until death or molting to the fifth instar. The results are summarized in the table below:

| | | SUPER IQ WITH BURLAP COLLARS | | | | | |
|---|---|---|---|---|---|---|---|
| | | Percent Mortality | | | | | |
| | | Days Post-Application | | | | | |
| Treatment | Rate | 7 | 14 | 27 | 28 | 31 | All Dates |
| Super IQ - WO | 0.046 ml/cm$^2$ | 74.8 a | 65.7 a | 91.0 a | 43.6 a | 64.3 a | 67.9 a |
| Super IQ - RO | 0.046 ml/cm$^2$ | 72.9 a | 47.3 a | 53.7 b | 53.6 a | 69.2 a | 59.1 a |
| Untreated Check - WO | — | 7.5 b | 13.3 b | 4.0 c | 0 b | 0 b | 5.0 b |
| Untreated Check - RO | — | 4.0 b | 0 b | 4.0 c | 7.5 b | 8.3 b | 4.5 b |
| Air Temperature during exposure (deg. C.) Means ± SE | | 25.4 ± 4.6 | 32.4 ± 2.1 | 25.0 ± 3.1 | 26.3 ± 4.5 | No data | |

Means within a column followed by the same letter are not significantly different (P = 0.05);
The caterpillars placed on the treated trees showed an average mortality rate of 63.5% as compared with the untreated tress that showed a mortality rate of 4.7%.

The caterpillars placed on the treated trees showed an average mortality rate of 63.5% as compared with the untreated tress that showed a mortality rate of 4.7%.

What is claimed is:

1. A method of controlling insect infestation comprising:
   providing an insecticide;
   providing a cover;
   coating at least a portion of a surface with said insecticide; and
   creating a darkened region on said surface by positioning said cover such that said cover shades said at least a portion of said surface coated with said insecticide.

2. A method as recited in claim 1 wherein said insecticide has a residual period of at least one month.

3. A method as recited in claim 1 wherein said insecticide contains an active ingredient selected from the group consisting of chlorpyrifos and pyrethroid.

4. A method as recited in claim 3 wherein said pyrethroid is tralomethrin.

5. A method as recited in claim 1 wherein said surface is at least one member selected from the group consisting of tree trunks, tree branches, and outer surfaces of structures.

6. A method as recited in claim 1 wherein said cover is selected from the group consisting of fabrics, wood, paper, cardboard, plastic and rubber.

7. A method as recited in claim 1 wherein said cover is comprised of burlap.

8. A method as recited in claim 1 wherein said cover is a barrier comprised of a flat back portion, a first flat side portion, and a second flat side portion, wherein said flat side portions are connected at each edge of width of said back portion and extend from said back portion.

9. A method as recited in claim 8 wherein said first and second side portions are the same length as said back portion.

10. A method as recited in claim 8 wherein said second side portion extends from said back portion farther than said first side portion.

11. A method as recited in claim 8 wherein said barrier further comprises end caps positioned at either end of the length of said back portion of said barrier to create a substantially darkened region.

12. A method as recited in claim 11 wherein said end caps are comprised of a center portion, and two side portions connected at opposite ends of said center portion.

13. A method as recited in claim 1 wherein said step of creating a darkened region comprises:
   providing a means for securing said cover to said surface; and
   releasably securing said cover to at least a portion of said surface.

14. A method as recited in claim 13 wherein said means for securing said cover to said surface is at least one member selected from the group consisting of staples, nails, rope, twine, tape and glue.

15. A method as recited in claim 3 wherein said pyrethroid is permethrin.

* * * * *